United States Patent [19]  [11] 4,009,274
Curran  [45] Feb. 22, 1977

[54] CERTAIN 3-PYRIDINECARBONITRILES, DERIVATIVES THEREOF AND ANTI-ULCER COMPOSITIONS CONTAINING SAME

[75] Inventor: Adrian Charles Ward Curran, North Humberside, England

[73] Assignee: John Wyeth & Brother Limited, Maidenhead, England

[22] Filed: Feb. 19, 1976

[21] Appl. No.: 659,433

Related U.S. Application Data

[63] Continuation-in-part of Ser. No. 468,726, May 10, 1974, Pat. No. 3,981,878, which is a continuation-in-part of Ser. No. 299,995, Oct. 24, 1972, Pat. No. 3,845,064.

[30]    Foreign Application Priority Data

Oct. 29, 1971    United Kingdom ............ 50431/71

[52] U.S. Cl. ............................ 424/263; 260/294.9; 260/294.8 E; 260/293.73; 260/293.75; 424/267
[51] Int. Cl.² ................ A61K 31/34; C07D 213/57
[58] Field of Search ................ 260/294.9; 424/263

[56]    References Cited

UNITED STATES PATENTS 3,551,432  12/1970  Wendler et al. ................ 260/294.9

*Primary Examiner*—Alan L. Rotman
*Attorney, Agent, or Firm*—Arthur E. Wilfond

[57]    ABSTRACT

The invention provides a compound of formula I

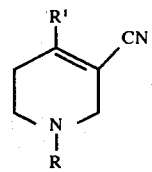

wherein R is phenylloweralkyl and $R^1$ is loweralkyl and the pharmaceutically acceptable acid addition salts thereof. Also included are anti-ulcer compositions comprising an effective amount of a compound of formula I and a pharmaceutically acceptable carrier.

5 Claims, No Drawings

CERTAIN 3-PYRIDINECARBONITRILES, DERIVATIVES THEREOF AND ANTI-ULCER COMPOSITIONS CONTAINING SAME

The invention relates to novel heterocyclic compounds and to pharmaceutical compositions containing them and is a continuation-in-part of my copending application 468,726 filed May 10, 1974 now U.S. Pat. No. 3,981,878 granted Sept. 21, 1976, which in turn is a continuation-in-part of my application Ser. No. 299,995 filed Oct. 24, 1972 now U.S. Pat. No. 3,845,064 issued Oct. 29, 1974.

This invention provides a compound of formula I

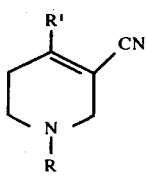

(I)

wherein R is phenylloweralkyl and $R^1$ is loweralkyl and the pharmaceutically acceptable acid addition salts thereof.

When $R^1$ is a lower alkyl radical it may be a straight or branched chain, having from 1 to 6 carbon atoms, e.g. methyl, ethyl, propyl or butyl but preferably has from 1 to 3 carbon atoms. When R is a phenyl-loweralkyl group the lower alkyl portion may be as discussed above for a lower alkyl group $R^1$. The alkyl groups may be substituted e.g. by a halogen atom or an alkoxy group.

The preferred phenyl groups for the phenyl portion of phenyl-alkyl group R may be substituted for example by a halogen atom, or an alkyl, alkoxy, nitro or haloalkyl (e.g. trifluoromethyl) radical.

The compounds of formula (I) can form acid addition salts with inorganic acids e.g. hydrochloric, hydrobromic, sulphuric and nitric acid or organic acids e.g. citric, fumaric, maleic and tartaric acid.

The compounds of formula I may be used in pharmaceutical compositions with a pharmaceutical carrier.

For the pharmaceutical carrier any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent, or a mixture of both. The active ingredient can often be dissolved in suitable organic solvent, for instance aqueous propylene glycol or polyethylene glycol solutions. Aqueous propylene glycol containing from 10 to 75% of the glycol by weight is generally suitable. In other instances compositions can be made by dispersing the finely divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

Compounds of formula I have been shown to possess pharmacological activity, namely anti-ulcer activity. The anti-ulcer activity was determined by the method of Brodie and Hanson, J. Applied Physiology, 15, 291, 1960, 1-Benzyl-1,2,5,6-tetrahydro-4-methyl nicotinonitrile showed good activity in this test at 30 and 100 mpk.

The anti-ulcer composition of the invention will be administered orally in either liquid or solid composition form. These compositions may include one or more antacid ingredients, e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

The compounds of formula I are also useful as intermediates for the preparation of compounds of formula II

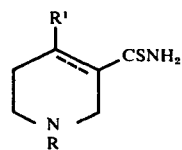

(II)

wherein R and $R^1$ are as defined in connection with formula I and the dotted line denotes an optional double bond. Compounds of formula II are described in application Ser. No. 299,995 (U.S. Pat. No. 3,845,064) as is their preparation from compounds of formula I. A compound of formula I wherein R and $R^1$ are as defined above may be treated with a thioamide of formula

where R⁴ is an alkyl group of 1–6 carbon atoms preferably a methyl group in dimethyl formamide saturated with hydrogen chloride to give the corresponding compound of formula II wherein R and R¹ are as defined above.

The nitriles of formula I may be prepared by reduction of a corresponding 3-cyanopyridine of formula (XI) wherein R and R¹ are as defined in connection with formula (I), and Z⁻ is an anion e.g. a halide ion.

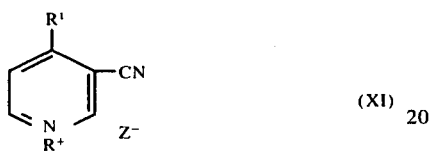

The reduction is conveniently carried out with a boro-hydride e.g. an alkali-metal borohydride especially sodium borohydride.

Another method of preparing nitriles of formula I comprises cyclising an open chain compound in the presence of a basic condensing agent. Any strong base will suffice such as an alkali metal alkoxide e.g. sodium methoxide or ethoxide, sodium amide or Triton B (benzyltrimethyl ammonium hydroxide). Thus a compound of formula (XII) wherein R and R¹ are as defined in connection with formula I

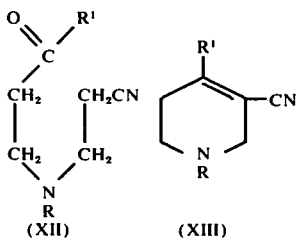

can be cyclised to a compound of formula (XIII). The reaction can be carried out in a suitable inert solvent e.g. benzene and the water removed by azeotropic distillation. Sometimes an intermediate compound of formula (XIV)

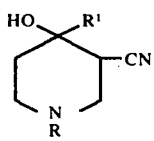

wherein R and R¹ are as defined in connection with formula (XII) is formed as a byproduct. This compound can be separated usually by fractional crystallisation but can be further dehydrated by heating to a compound of formula (XIII) if desired. Often distillation of the crude product of the cyclisation reaction will suffice to effect dehydration of XIV.

A nitrile in which R is aralkyl may be prepared by aralkylation of a corresponding compound where R is hydrogen using standard aralkylating conditions. Thus a compound of formula (XV) wherein R¹ is as defined in connection with formula I can be aralkylated

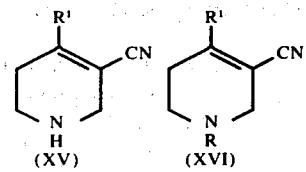

to give a compound of formula (XVI) wherein R is aralkyl. The starting compound of formula (XV) can be prepared from compound (XII) as defined above, where R is hydrogen.

Methods of preparing the novel nitriles of the invention are also included in the invention.

The following examples illustrate the invention:

EXAMPLE 1

1-Benzyl-1,2,5,6-tetrahydro-4-methylnicotinonitrile

A mixture of β-cyanoethylbenzylamine (92 g.), conc hydrochloric acid (60 ml.), ethanol (120 ml.), paraformaldehyde (30 g.) and acetone (120 ml.) were heated at reflux for 5 hours. The solvent was removed in vacuo and the residue dissolved in water (100 ml.) and washed with ether (2 × 100 ml.). The aqueous solution was made basic with aqueous potassium carbonate and the solution extracted with ether (3 × 100 ml.). The combined extracts were dried and evaporated to give N-benzyl-N-(2-cyanoethyl)-4-aminobutan-2-one (132 g) which was dissolved in dry benzene (1.3 liter) and sodium methoxide (prepared from sodium (13.2g) was added portionwise. The mixture was refluxed for 5 hours and the cooled solution washed with 2N HCl (4 × 500 ml.). The combined extracts were made basic with potassium carbonate and extracted into methylene chloride (4 × 500 ml.) and the combined extracts dried (MgSO₄) and solvent removed in vacuo. The residual oil was distilled to give 1-benzyl-3-cyano-4-methyl-1,2,5,6-tetrahydropyridine as a colourless oil (40 g.) b.p. 136° C/5 × 10⁻³mm. Hg. which was converted to the hydrochloride by treating an ethereal solution with dry HCl gas. The resultant solid was recrystallised from methanol-ether giving the hydrochloride of the title compound as colourless needles (35 g.) m.p. 172° C. Found: C, 68.0; H, 7.0; N, 11.3% C₁₄H₁₆ N₂HCl requires C, 67.6; H, 6.9; N, 11.3%.

EXAMPLE 2

| Suspension | % w/v |
| --- | --- |
| Aluminium hydroxide gel B.P. 5% Al₂O₃ | 80% = 4% Al₂O₃ |
| Magnesia Magma 12% w/v MgO | 10% |
| 1-Benzyl-1,2,5,6-tetrahydro-4-methylnicotinonitrile | 2.0% |
| Glycerin B.P. | 3.0% |
| Alcohol 60 O.P.* | 0.08% |
| Peppermint oil B.P. | 0.015% |
| Saccharin sodium B.P. | 0.01% |
| Methyl p-hydroxybenzoate sodium salt | 0.1% |
| Propyl p-hydroxybenzoate sodium salt | 0.02% |
| Butyl p-hydroxybenzoate sodium salt | 0.01% |
| Water q.s. ad | 100.00% |

*O.P. denotes overproof. 60 O.P. represents 91% w/v Ethanol/water.

The above suspension is prepared by the following procedure. Add to the Alumina gel Magnesia Magma followed by the 1-benzyl-1,2,5,6-tetrahydro-4-methylnicotinonitrile dispersed in alcohol, the saccharin sodium dissolved in water, and the p-hydroxybenzoates dissolved in water. Make up to volume with water and stir well. Dose: 5 ml. t.d.s.

EXAMPLE 3

| Antacid Tablet (chewable). | |
|---|---|
| Saccharin | 1.0 mg. |
| Hydrated alumina sucrose powder | 750.0 mg. |
| 1-Benzyl-1,2,5,6-tetrahydro-4-methyl nicotinonitrile | 100.0 mg. |
| Mannitol B.P. | 170.0 mg. |
| Maize starch B.P. dried | 30.0 mg. |
| Talc. purified B.P. | 28.0 mg. |
| Magnesium stearate B.P. | 20.0 mg. |
| Peppermint oil B.P. | 1.0 mg. |
| | 1100.0 mg. |

Antacid tablets of the above formulation are prepared by the following procedure.

Triturate peppermint oil with talc (screen 40 mesh).
Add the triturate, and other ingredients to a blender and mix thoroughly.
Slug the powder to large hard slugs.
Granulate the slugs through a 14 mesh screen.
Compress the granules on a suitable compression machine to give tablets of the required size.

EXAMPLE 4

| Anti-ulcer tablet (without antacid). | |
|---|---|
| | mg/tablet |
| 1-Benzyl-1,2,5,6-tetrahydro-4-methyl nicotinonitrile | 100 mg. |
| Celutab | 147.5 mg. |
| Mag. Stearate | 2.5 mg. |
| | 250.0 mg. |

The tablets are prepared by the following method. Blend the ingredients in a suitable blender. Compress the blended ingredients on a suitable compression machine to form tablets of the above composition.

Celutab is a commercial product comprising 90–2% dextrose, 3–5% maltose remainder higher glucose saccharides. Spray crystallised.

I claim:
1. An anti-ulcer composition comprising an effective amount of a compound of formula

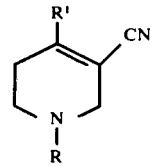

wherein R is phenylloweralkyl and $R^1$ is loweralkyl or a pharmaceutically acceptable acid addition salt thereof and a pharmaceutically acceptable carrier.

2. An anti-ulcer composition as claimed in claim 1 in unit dosage form.

3. An anti-ulcer composition as claimed in claim 1 wherein the compound of formula I is 1-benzyl-1,2,5,6-tetrahydro-4-methylnicotinonitrile.

4. A compound of formula

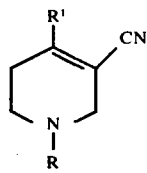

wherein R is phenylloweralkyl and $R^1$ is lower alkyl or a pharmaceutically acceptable acid addition salt thereof.

5. 1-Benzyl-1,2,5,6-tetrahydro-4-methylnicotinonitrile or a pharmaceutically acceptable acid addition salt thereof.

* * * * *